US005770440A

United States Patent [19]
Berndt

[11] Patent Number: 5,770,440
[45] Date of Patent: Jun. 23, 1998

[54] APPARATUS FOR THE EARLY DETECTION OF MICROORGANISMS

[75] Inventor: Klaus W. Berndt, Stewartstown, Pa.

[73] Assignee: Becton Dickinson and Company, Franklin Lakes, N.J.

[21] Appl. No.: 850,590

[22] Filed: May 2, 1997

Related U.S. Application Data

[63] Continuation of Ser. No. 495,157, Jun. 27, 1995.

[51] Int. Cl.⁶ ..................................................... C12M 3/00
[52] U.S. Cl. .................................. 435/288.4; 435/288.5; 435/288.7; 435/808
[58] Field of Search ........................... 435/288.3, 288.4, 435/288.5, 288.7, 808

[56] References Cited

U.S. PATENT DOCUMENTS

| 5,252,294 | 10/1993 | Kroy et al. ............................... 422/102 |
| 5,293,210 | 3/1994 | Berndt ........................................ 356/39 |
| 5,310,658 | 5/1994 | Berndt ........................................ 435/34 |
| 5,340,747 | 8/1994 | Eden .......................................... 436/172 |
| 5,371,016 | 12/1994 | Berndt ...................................... 435/291 |
| 5,397,709 | 3/1995 | Berndt ........................................ 436/34 |
| 5,427,920 | 6/1995 | Berndt et al. ............................. 435/34 |
| 5,432,061 | 7/1995 | Berndt et al. ............................. 435/34 |
| 5,473,437 | 12/1995 | Blumenfeld et al. .................. 356/417 |
| 5,485,277 | 1/1996 | Foster ...................................... 356/445 |

OTHER PUBLICATIONS

Difco Laboratorie Jan. 1994 Product Catalog for Microbiology, pp. 65, 68, 69.

*Primary Examiner*—David A. Redding
*Attorney, Agent, or Firm*—Alan. W. Fiedler

[57] ABSTRACT

The present invention describes an apparatus for detecting microorganisms in a culture container. The container includes a block having a plurality of through holes for dividing the sample into a plurality of partial samples. Each partial sample has its own head space and its own sensor. The spacial array of partial samples is read out by a CCD camera and split into partial sample to generate a spacial array that results in a substantial reduction in the time to detection.

10 Claims, 13 Drawing Sheets

APPARATUS FOR THE EARLY DETECTION OF MICROORGANISMS

This application is a continuation of application Ser. No. 08/495,157, filed Jun. 27, 1995 now abandoned.

BACKGROUND OF THE INVENTION

1. Field of the Invention

The present invention relates to a method and apparatus for reducing the time to detection (TTD) of biological activity in blood cultures and for mycobacteria in body fluids.

2. Background Description

The presence of biologically active agents such as bacteria in a patient's body fluid, especially blood, is generally determined using blood culture vials. A small quantity of blood is injected through an enclosing rubber septum into a sterile vial containing a culture medium, and the vial is then incubated at 37° C. and monitored for microorganism growth.

One of the techniques used to detect the presence of microorganisms includes visual inspection. Generally, visual inspection involves monitoring the turbidity or eventual color changes of the liquid suspension of blood and culture medium. Known instrumental methods detect changes in the carbon dioxide content of the culture bottles, which is a metabolic by-product of the bacterial growth. Monitoring the carbon dioxide content can be accomplished by methods well established in the art, such as radiochemical or infrared absorption at a carbon dioxide spectral line. Until now, these methods have required invasive procedures which result in the well-known problem of cross-contamination between different vials. It has also been proposed to detect microorganism growth in sealable containers by monitoring positive and/or negative pressure changes.

Recently, non-invasive methods have been developed involving chemical sensors disposed inside the vial. These sensors respond to changes in the carbon dioxide concentration by changing their color or by changing their fluorescence intensity. In known automated non-invasive blood culture systems, individual light sources, spectral excitation/emission filters, and photodetectors are arranged adjacent to each vial. This results in station sensitivity variations from one vial to the next. Additional problems are caused by the aging effects of the light sources, filters and photodetectors. Due to the fact that most known blood culture sensors generate only a moderate contrast ratio in the measured photocurrent during bacterial growth, extensive and time-consuming calibration procedures and sophisticated detection algorithms are required to operate these systems. In addition, flexible electrical cables are required to connect the individual sources and detectors with the rest of the instrument. With the large number of light sources, typically 240 or more per instrument, maintenance can become very cumbersome and expensive when individual sources start to fail.

The disadvantage of intensity-based sensor arrangements can be overcome by utilizing fluorescent sensors that change their lifetime. In this case, intensity measurement is replaced with time parameter measurement, and intensity changes have no impact on the sensor output signal. Many chemical sensor materials are known that change their fluorescence lifetime with changing oxygen concentration, pH, carbon dioxide concentration, or other chemical parameters.

The change in the sensor fluorescence lifetime is commonly monitored by applying the well-known phase shift method. In this method, the excitation light is intensity-modulated, which results in an intensity-modulated fluorescence emission that is phase-shifted relative to the excitation phase. The phase shift angle, $\theta$, is dependent on the fluorescence lifetime $\tau$, according to the equation.

$$\tan\theta = \omega\tau \quad (1)$$

where $\omega = 2\pi f$ is the circular light modulation frequency.

An inspection of equation (1) reveals that the phase shift method allows for maximum resolution, $d\theta/d\tau$, under the condition $\omega\tau = 1$. Unfortunately, almost all known pH- or carbon dioxide-sensitive fluorophores have decay times in the range 5 ns to 500 ps. In other words, light modulation frequencies, $f = \frac{1}{2}\pi\tau$, in the range 32 MHz to 320 MHz would be required.

It is possible to accomplish light intensity modulation at such high frequencies, but that requires acousto-optic or electro-optic modulators that are only efficient in combination with lasers. Moreover, detecting the modulated fluorescence light would require high-speed high-sensitivity photodetectors such as microchannel-plate photomultipliers, which are rather expensive. Consequently, all commercial automated blood culture systems are based on intensity monitoring, and none of them utilize time-resolved fluorescent carbon dioxide sensors.

Even if it would be possible to operate fluorescence lifetime-based sensors at low cost, all sample-related artifacts would remain. In particular, the so-called "blood-background effect" has to be mentioned which is a continuous but unpredictable change in the fluorescence intensity and/or lifetime due to the metabolism of the blood itself. Because the blood-background effect can depend on the donor, the growth medium, the blood volume, and other factors, it is very difficult or impossible to distinguish between blood-related and organism-related fluorescence changes. Consequently, the detection algorithms have to be "robust" which results in a relatively long time to detection.

SUMMARY OF THE INVENTION

The present invention overcomes the above problems and comprises a method and apparatus for detecting biologically active agents that allows for a short time to detection, even in the presence of common instrumental and sample-related artifacts.

According to the present invention, the above objective is achieved by introducing a standard amount of specimen such as blood and a growth medium into a sealable container, and mixing the specimen with the growth medium inside the container. The container is designed so that by acting on the container from the outside, the liquid sample inside the container is divided into a number of partial samples with each partial sample having its own headspace and its own sensing means. The number of partial samples, N, is chosen to be larger than the number of primary microorganisms expected to be within the sample at the time it was introduced it into the container.

Compared to a standard blood culture container, the number of microorganisms necessary to cause a typical change in gas concentration or in other parameters within a partial sample is reduced N times when the volume is reduced N times. As a consequence, less microorganisms are required in a partial sample to cause a measurable change in a sensor output signal. Therefore, a first reduction of the time to detection is achieved.

According to the present invention, all the partial samples are arranged in a spacial array, which can be linear, circular, rectangular, hexagonal, statistically distributed, or may have other forms. The sensor signals of all partial samples are compared with each other, either visually or by means of an instrument. Microorganism growth in one or more than one partial sample causes a change in the sensor signal, relative to partial samples that do not contain microorganisms. A whole sample is then considered positive if at least one partial sample generates a sensor signal that is different from the signals generated by its neighbors. In this way, measurement of sensor signal versus time is transferred into measurement of sensor signal versus distance.

All the partial samples that do not contain microorganisms act as "reference samples," i.e., they display all the artifacts that are caused by the instrument, sample aging, and temperature variations within the instrument. In particular, the reference samples display the so-called "blood-background effect." Due to the fact that in an apparatus according to the present invention only spacial differences in the sensor signals are indicative of microorganism growth, all the artifacts are canceled out, and a significantly improved sensor signal resolution becomes practical. Therefore, a second reduction of the time to detection ("TTD") is obtained.

Both TTD reductions provide a substantial improvement over existing growth-based systems. For example, a TTD of 72 hours can be shortened to 12 hours. In case of mycobacteria (TB), a TTD of 35 days can be shortened to 5 days.

In an apparatus according to the present invention, it is not necessary to execute measurements of the sensor signals versus distance at regular time intervals. Therefore, breaks in acquiring data due to door openings for the purpose of loading and unloading of samples has no negative effect. As mentioned above, the effect of temperature fluctuations due to door openings is also canceled out, and it becomes much easier to check so-called "delayed" vials for positivity, because positivity generates a permanent intensity-versus-distance pattern that can be read out at any time.

It is also possible to equip each partial sample with at least two different sensing means, which allows for microorganism identification in addition to detection by analyzing different sensor data.

These and other aspects, features and advantages of the present invention will become apparent from the following detailed description, taken in conjunction with the accompanying drawings.

DETAILED DESCRIPTION

According to the present invention, a standard amount of specimen such as blood and growth medium is introduced into a sealable container and mixed together thoroughly. If the sample comprises a small number of microorganisms, $K_O$, immediately after inoculation, then the number of microorganisms, $K(t)$, at a later time, t, is given by the equation $$K(t) = K_o \exp\left( \frac{\ln 2t}{t_d} \right) \quad (2)$$

with $t_d$ being the doubling time of the particular microorganism species present in the sample.

Usually, a certain minimum concentration of microorganisms per unit volume, $C_{min}$, is required within the container to produce a detectable change in the sensor output signal. The minimum concentration $C_{min}$, is related to a minimum number of microorganisms, $K_{min}$, via the equation $$K_{min} = C_{min} V_O \quad (3)$$

wherein $V_O$ is the volume of the whole container.

In an apparatus according to the present invention, the sample of volume $V_O$ is split into N separated subunits of value V by acting on the sample container from the outside. The volume V is $$V = \frac{V_o}{N}. \quad (4)$$

By combining equations (2) to (4), we obtain the time to detection, TTD, that is required for a microorganism population within a subunit of volume V to reach the minimum concentration $C_{min}$ $$TTD = t_d \frac{\ln\left(K_{min}\frac{V}{V_o}\right)}{\ln 2}. \quad (5)$$

In deriving equation (5), we have assumed that only one single microorganism was present within the subunit after inoculation, i.e., we have set $K_O=1$. Also, we have neglected the so-called "lag phase," i.e., a certain time interval the microorganisms usually need to start multiplying after inoculation.

Assuming a container of quadratic format with n rows and n columns of subunits, we obtain with $$N = n^2 \quad (6)$$

for the time to detection of a container according to the present invention $$TTD = t_d \frac{\ln \frac{K_{min}}{n^2}}{\ln 2} \quad (7)$$

Figure 1:
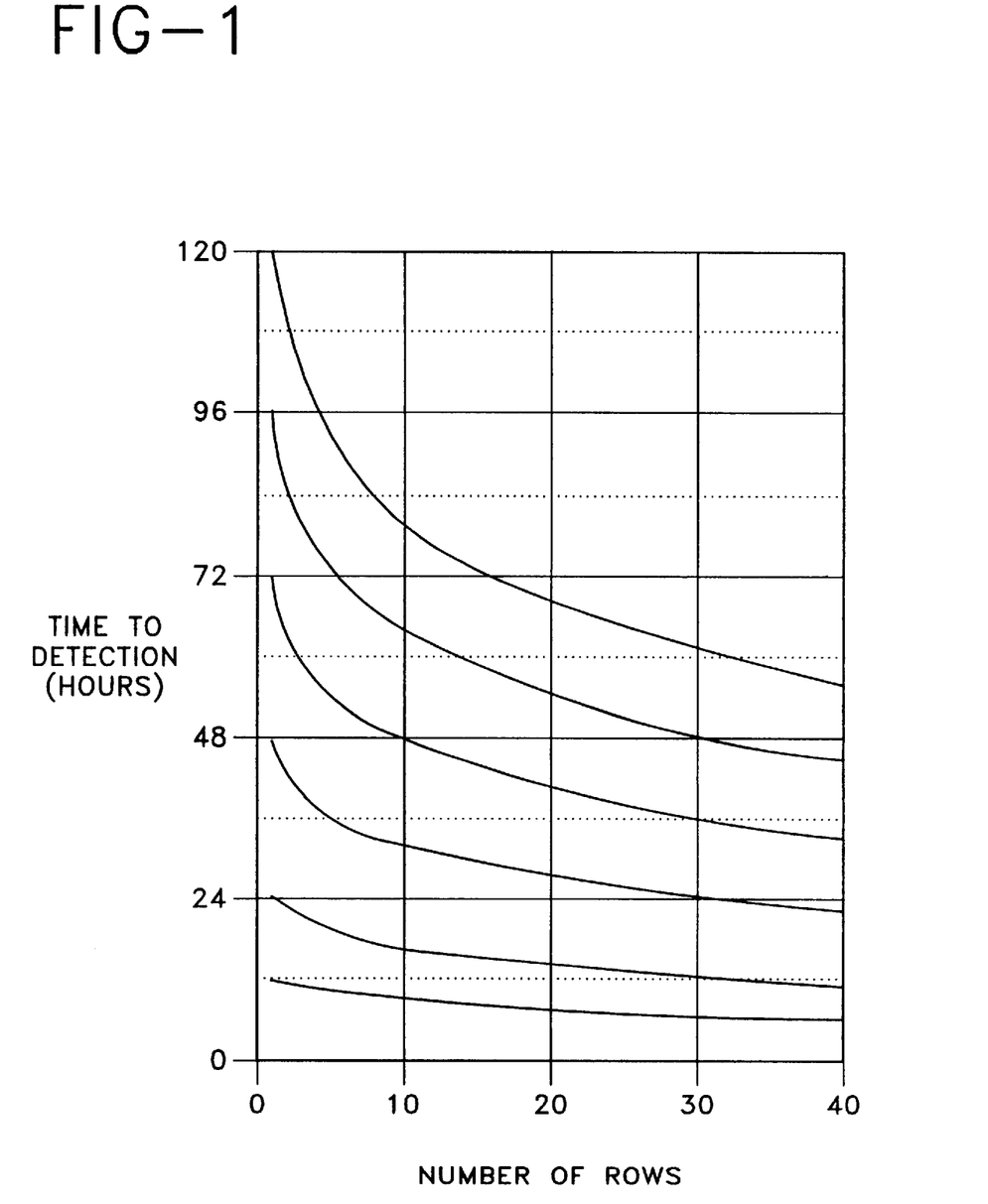
FIG. 1 shows a plot depicting calculated TTD for bacteria versus the number of rows of partial samples, assuming a quadratic format of a two-dimensional array.

FIG. 1 depicts a family of plots showing the time to detection, TTD, versus the number of rows, n, according to equation (7). The different curves correspond to different kinds of microorganisms with typical TTD values of 120, 96, 72, 48, 24 and 12 hours measured in ordinary growth-based blood culture instruments. These TTD values correspond to n=1, i.e., to one row and one column in FIG. 1.

As can be seen from FIG. 1, the usual TTD value can be reduced significantly by splitting a sample container according to the present invention into a number of subunits. The time savings are more pronounced for long TTD values. A common TTD of 120 hours would be reduced to 56 hours, using a sample container with 40 rows and 40 columns. In other words, the TTD would be reduced by 64 hours or 2.66 days. The time savings would be only 6 hours for a common TTD of 12 hours.

Figure 2:
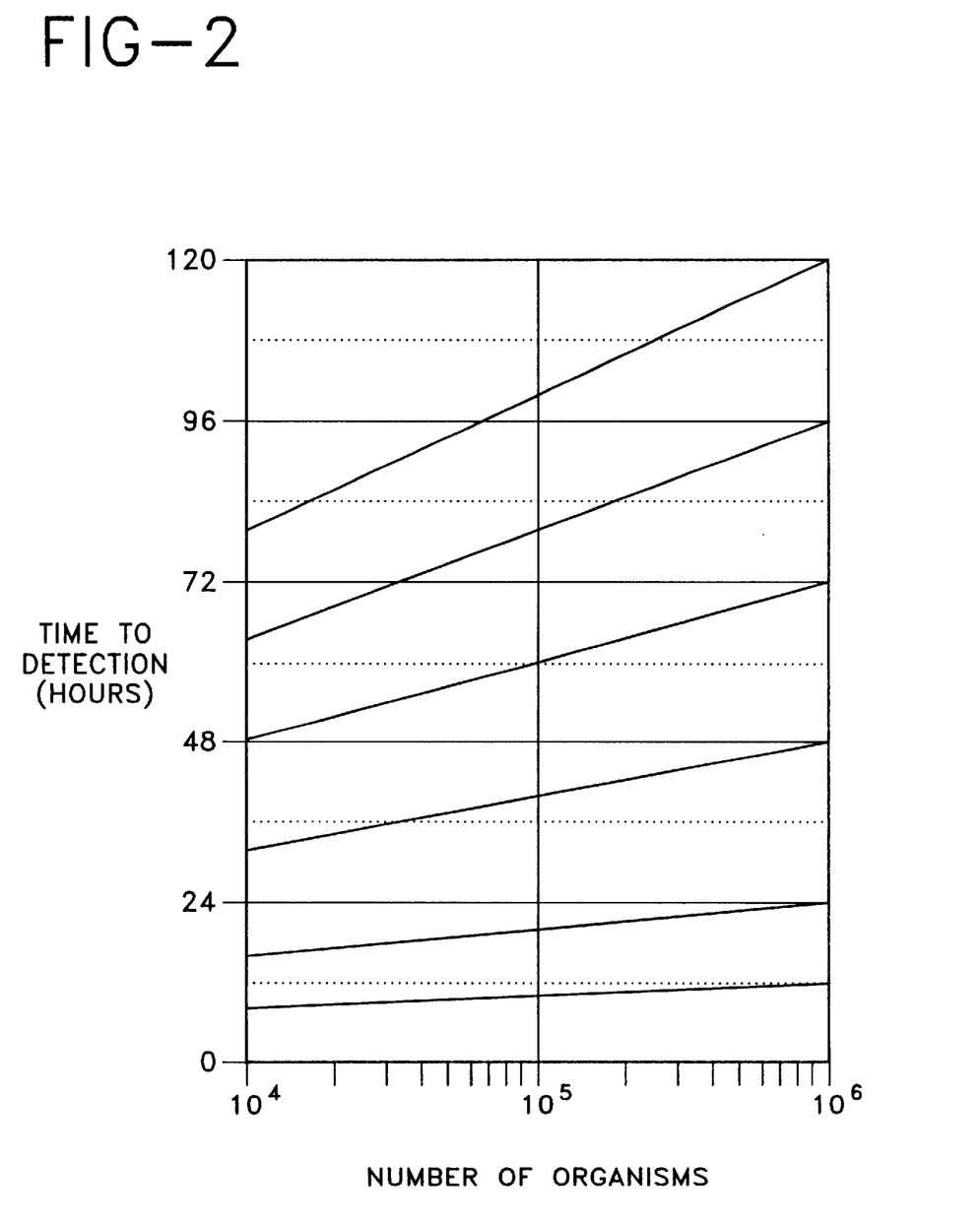
FIG. 2 shows a plot depicting calculated TTD for bacteria versus the number of organisms that are required to accomplish detection.

FIG. 2 illustrates a second advantage obtained by using a sample container according to the present invention. This is a reduction in the number of organisms required for detection, due to an increased sensor signal resolution. Because of the almost complete cancellation of commonly experienced artifacts, it appears feasible to reduce the required number of organisms by one or two orders of magnitude. FIG. 2 depicts plots showing the expected effect on the TTD if a common number $K_{min}=10^6$ could be reduced down to $10^5$ or even to $10^4$.

Figure 3:
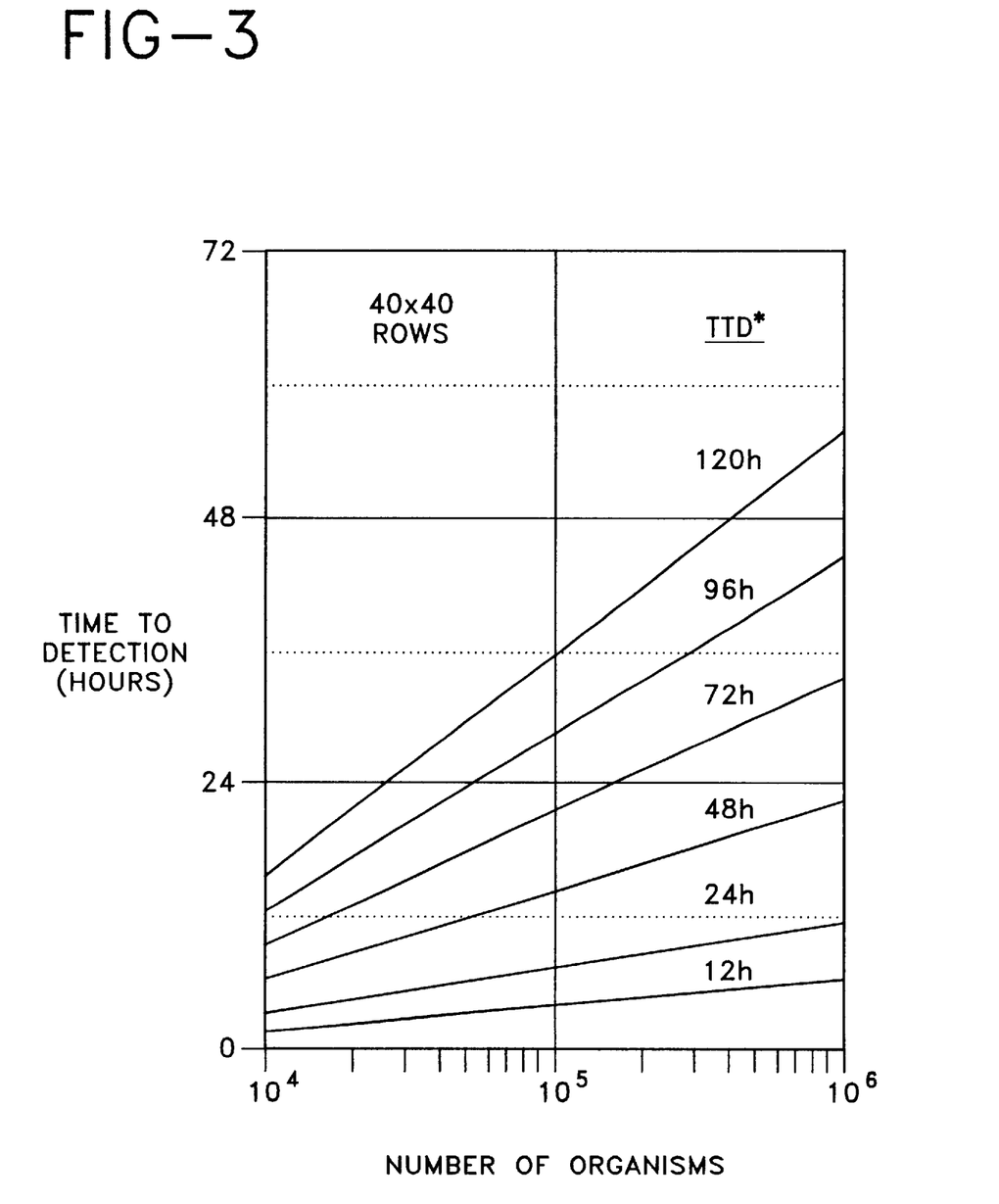
FIG. 3 shows a plot depicting calculated TTD for bacteria versus the number of organisms that are required to accomplish detection, taking into account the reduction in TTD achieved by splitting the sample into 40×40 partial samples.

FIG. 3 shows the combined effects of splitting the sample into 40×40 subunits, and decreasing the number of required organisms. As can be seen from this figure, a common TTD of 120 hours can be shortened to 16 hours, corresponding to a time savings of 104 hours or 4.33 days. A common TTD of 12 hours can be shortened to 2 hours. It has to be emphasized that FIGS. 1, 2 and 3 show calculated TTD values. Due to the fact that a second component contributing to the overall TTD, i.e., the lag phase, has been neglected in the analysis, the actual time savings for fast-growing microorganisms will be less than the calculated ones.

Figure 4:
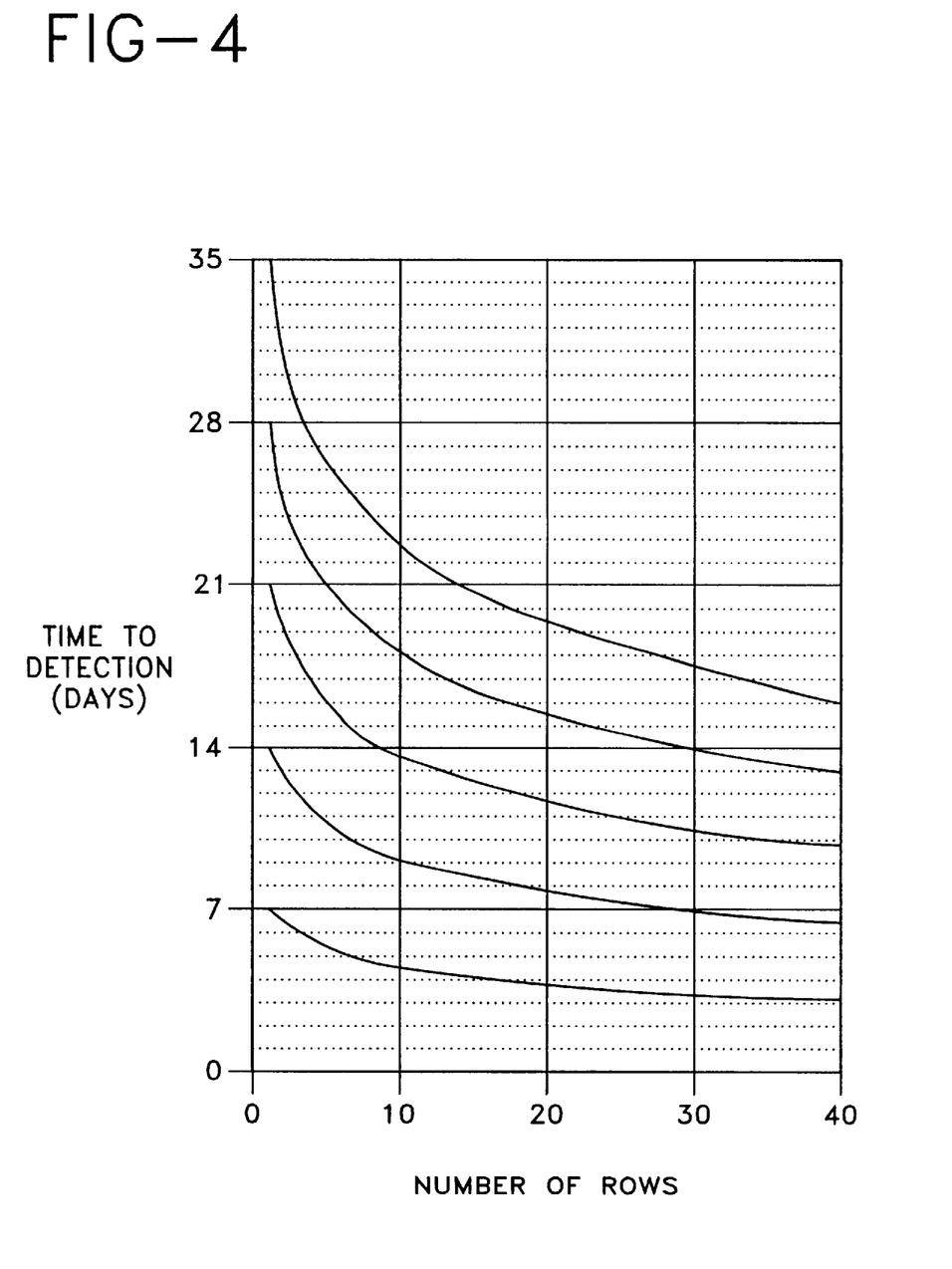
FIG. 4 shows a plot depicting calculated TTD for mycobacteria versus the number of rows of partial samples, assuming a quadratic format of the two-dimensional array.

FIG. 4 depicts a family of plots showing the time to detection, TTD, for mycobacteria versus the number of rows, n, according to equation (7). The different curves correspond to different kinds of mycobacteria with typical TTD values of 35, 28, 21, 14 and 7 days, measured in conventional growth-based TB culture instruments. Again, these TTD values correspond to n=1, i.e., to one row and one column in FIG. 4.

As can be seen from FIG. 4, the usual TTD value can be reduced significantly by splitting a sample container into a number of subunits. As in the case of bacteria, the time savings are more pronounced for long TTD values. A common TTD of 35 days would be reduced to 16 days, using a sample container with 40 rows and 40 columns. In other words, the TTD would be reduced by 19 days. The time savings would be 4 days for a common TTD of 7 days.

Figure 5:
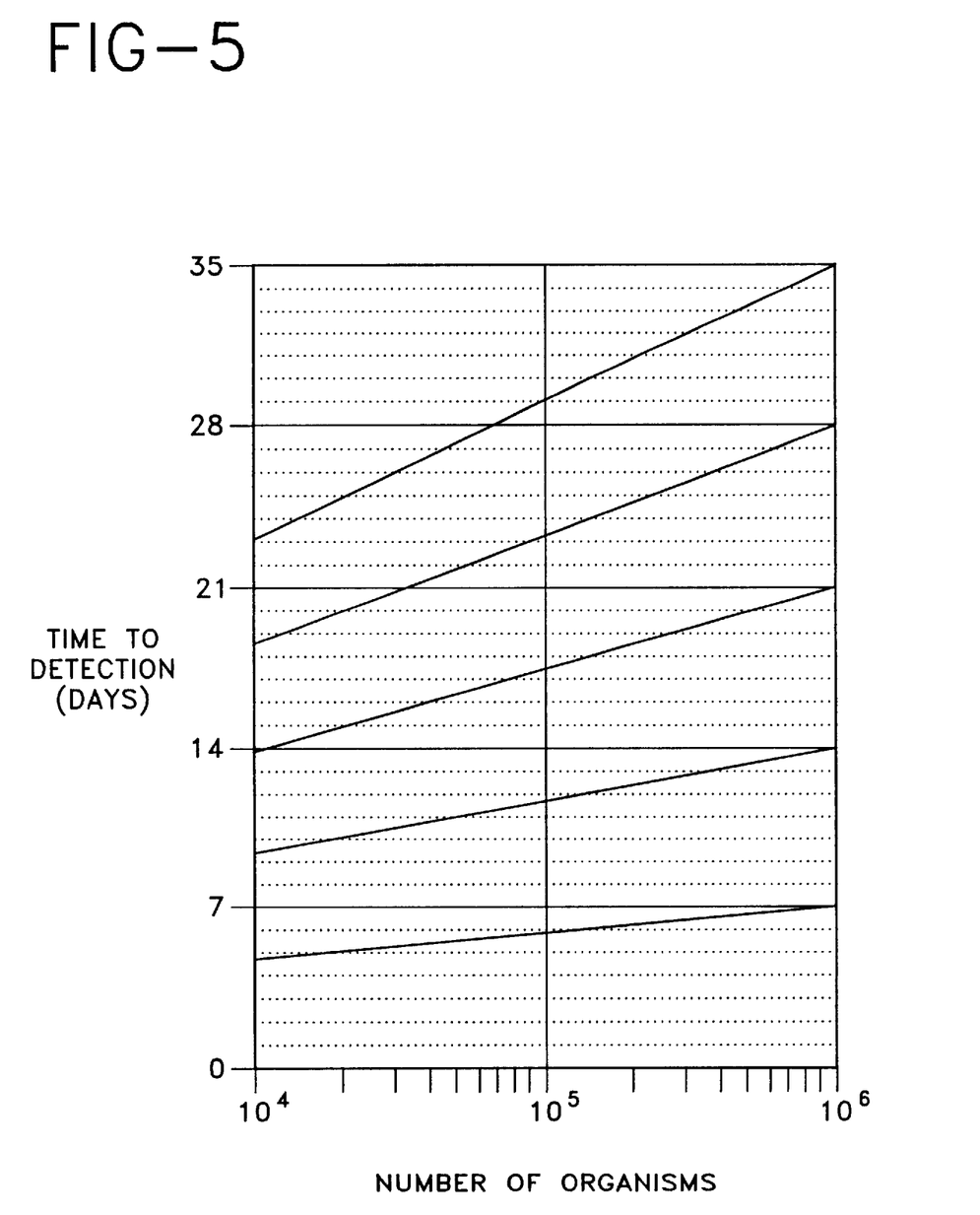
FIG. 5 shows a plot depicting calculated TTD for mycobacteria versus the number of organisms that are required to accomplish detection.

FIG. 5 illustrates the second advantage of a sample container according to the present invention for mycobacteria, i.e., a reduction in the number of organisms required for detection. FIG. 5 depicts plots showing the expected effect on the TTD if a common number $K_{min}=10^6$ could be reduced down to $10^5$ or even to $10^4$.

Figure 6:
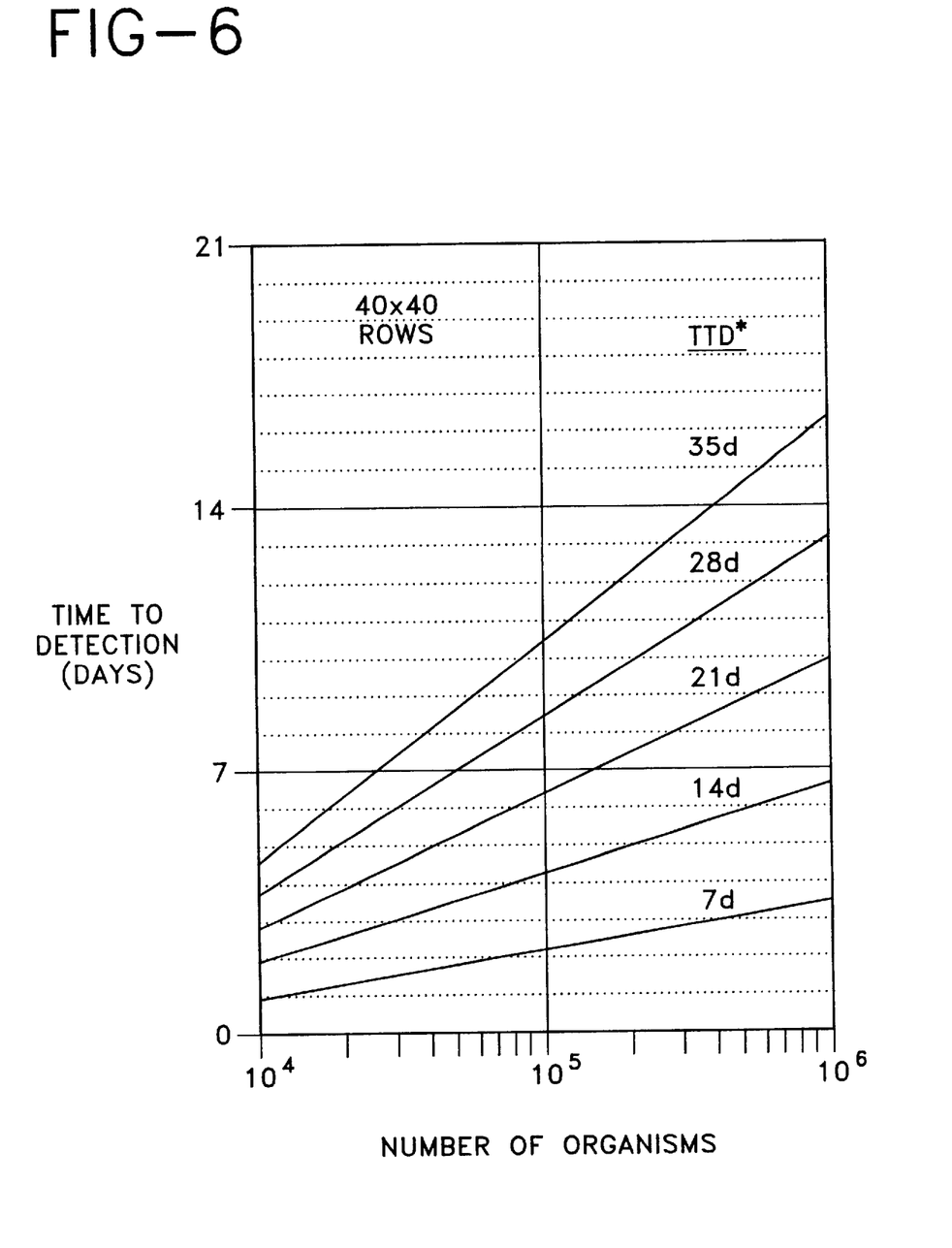
FIG. 6 shows calculated TTD for mycobacteria versus the number of organisms that are required to accomplish detection, taking into account the reduction in TTD achieved by splitting the sample into 40×40 partial samples.

FIG. 6 shows the combined effects of splitting the sample into 40×40 subunits, and decreasing the number of the required organisms. As can be seen from FIG. 6, a common TTD of 35 days can be shortened to 5 days, corresponding to a time savings of 30 days. A common TTD of 7 days can be shortened to 1 day. Again, it has to be emphasized that FIGS. 4, 5 and 6 show calculated TTD values and that actual time savings may be less than the calculated ones.

Figure 7:
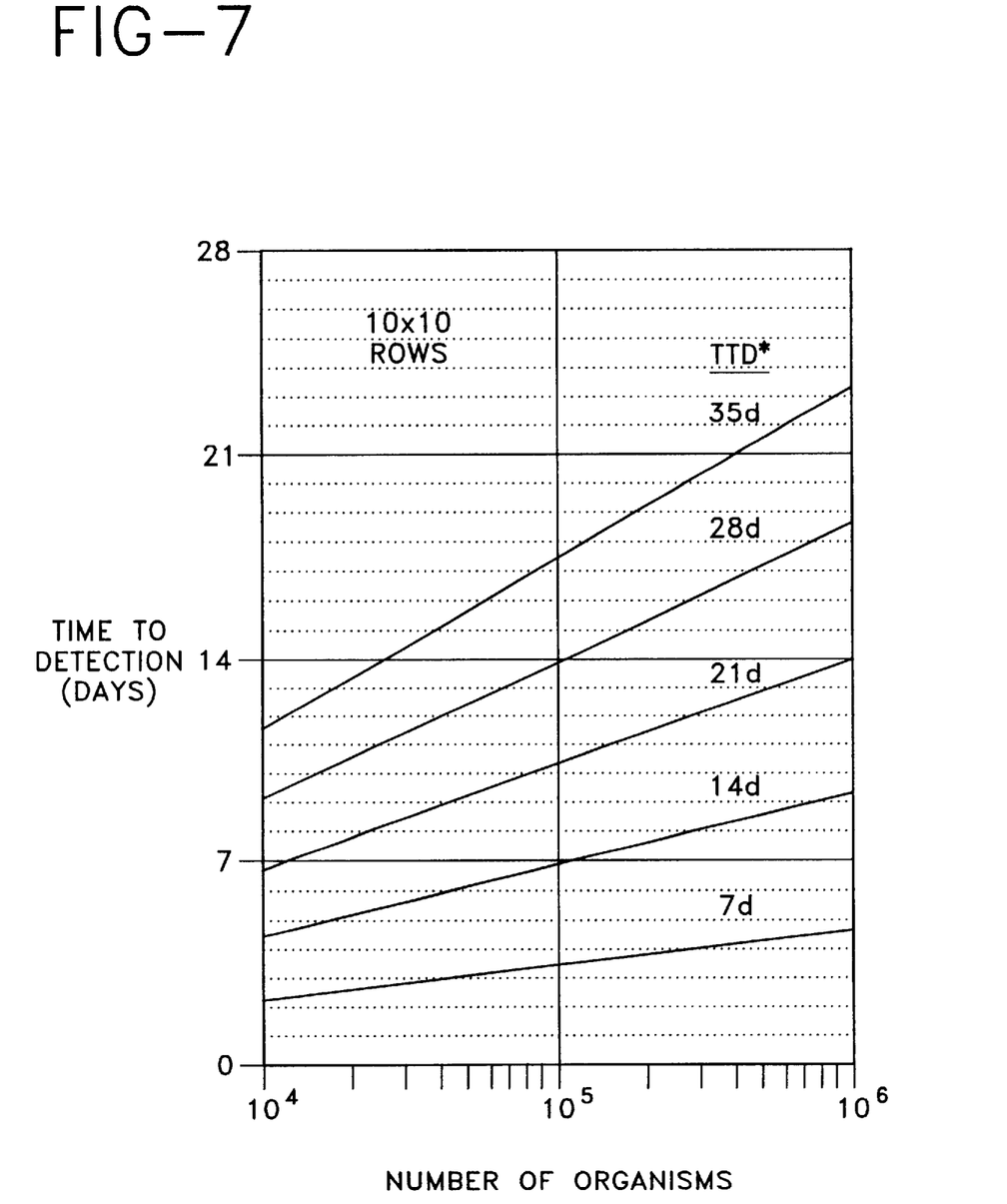
FIG. 7 shows calculated TTD for mycobacteria versus the number of organisms that are required to accomplish detection, taking into account the reduction in TTD achieved by splitting the sample into 10×10 partial samples.

FIG. 7 corresponds to FIG. 6, but shows the expected reductions in the TTD for a quadratic sample container with only 10×10 subunits. Even with such a low number of rows, a typical TTD of 35 days can be reduced to only 12 days.

Figure 8:
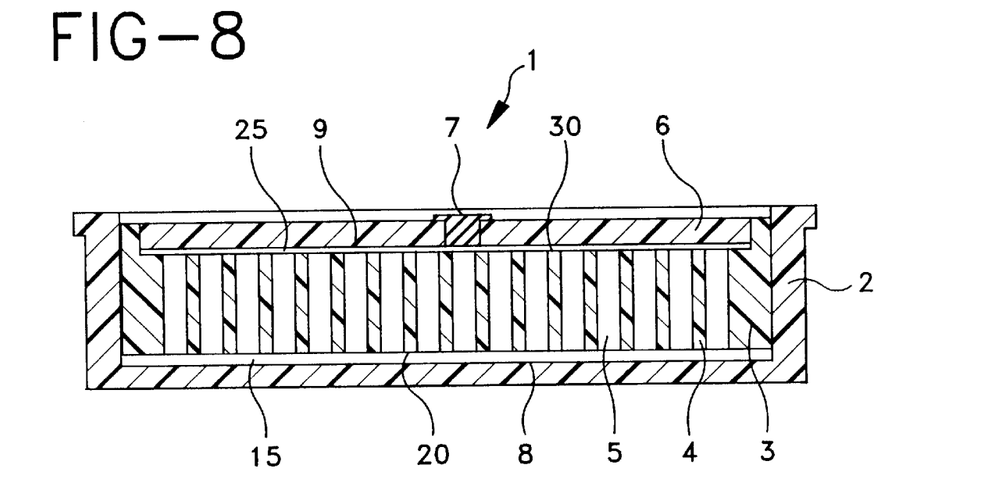
FIG. 8 shows a cross-section of any empty sample container according to the present invention.

A cross-sectional view of a sample container 1 embodying the principles and concepts of the invention is shown in FIG. 8. A specimen and culture medium are introduced into an optically transparent container 2 having an elastic block 3. Block 3 fits tightly into container 2 and comprises a plurality of through holes 5 that are separated by inner walls 4 and arranged in a regular pattern. Block 3 can be made out of rubber, soft plastic, or other elastic materials.

A cover plate 6 with a rubber-like septum 7 is pressed into the top of block 3 in such a way that no gas exchange can take place between the interior of container 2 and the outside environment. Block 3 is pressed into container 2 only so far that a small gap 15 remains between a lower surface 20 of block 3 and an inner bottom surface 8 of container 2. Cover plate 6 is pressed into block 3 only so far that a small gap 25 remains between a lower surface of cover plate 6 and an upper surface 30 of block 3. The sealed container 2 is filled with a culture gas having a sub-atmospheric pressure level, and is sterilized.

Figure 9:
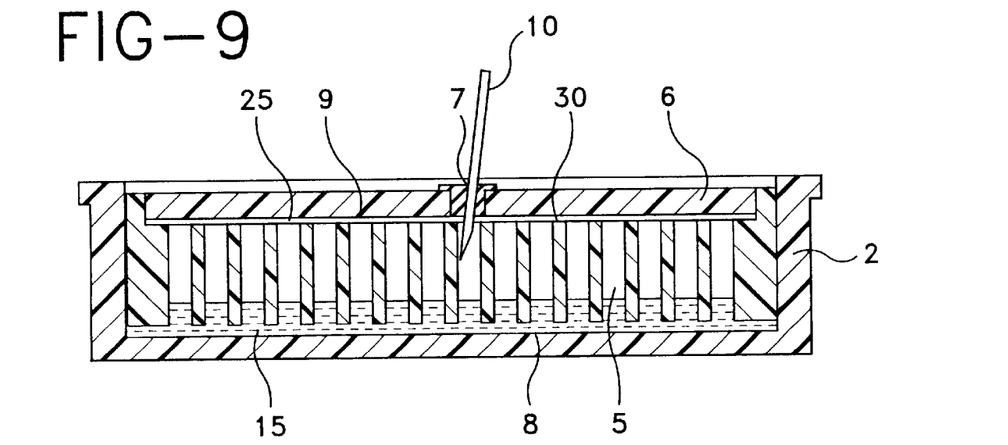
FIG. 9 shows a cross-section of a sample container during the process of injecting the sample.

FIG. 9 shows container 2 during the process of inoculating it with a culture medium and/or a microorganism sample. Inoculation is accomplished using a syringe 10 which penetrates rubber septum 7. During the inoculation procedure, container 2 is held in a horizontal orientation and because of the above-mentioned gaps 15 and 25, the culture medium and sample mixture is distributed evenly on the inner bottom surface 8 of container 2.

Figure 10:
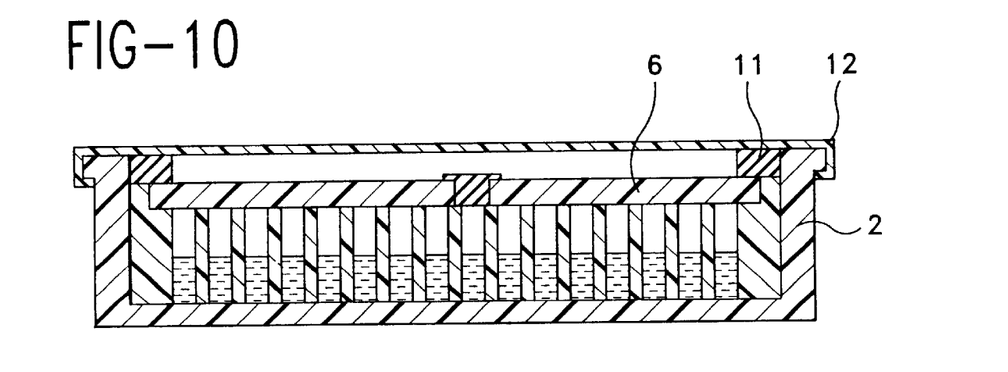
FIG. 10 shows a cross-section of a sample container after injecting the sample and applying an external force to split the sample.

According to the present invention, an external force is then applied to cover plate 6 after inoculating the microorganism sample. Due to the external force, cover plate 6 moves towards upper surface 30 of block 3, and block 3 moves towards inner bottom surface 8 of container 2. As a result, the liquid sample is pressed into through holes 5 of block 3, and forms a plurality of separated partial samples that have their own head spaces. FIG. 10 shows sample container 1 after applying the external force, with cover plate 6 and block 3 being kept in place by means of a simple locking mechanism comprising a semi-rigid frame 11 and one or two clips 12.

Figure 11A:
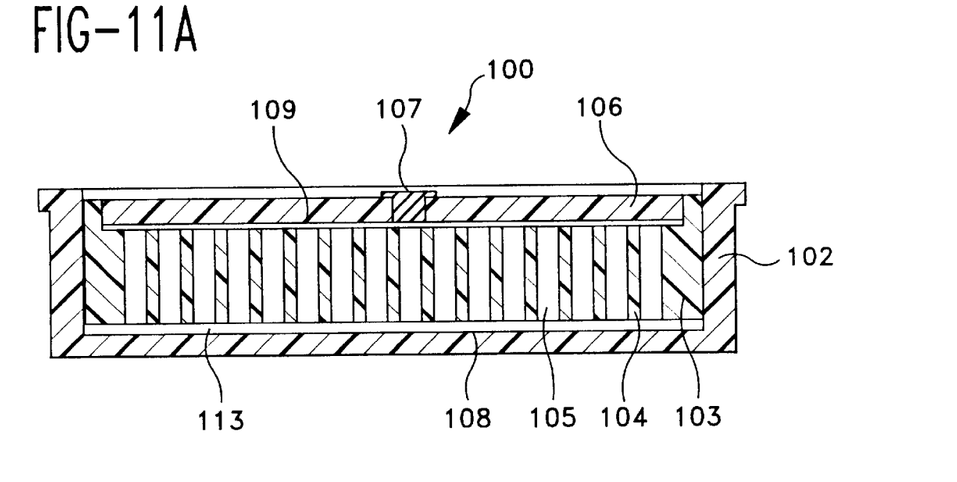
FIG. 11A shows a cross-section of an empty sample container having a fluorescent chemical sensor.

FIG. 11A illustrates a sample container 100 with a fluorescent chemical sensor 113 evenly disposed onto an inner bottom surface 108 of a container 102. In order to interrogate a sample container 100 for microorganism growth, the bottom surface 108 of container 102 is illuminated with an excitation light and monitored by a CCD camera.

Figure 11B:
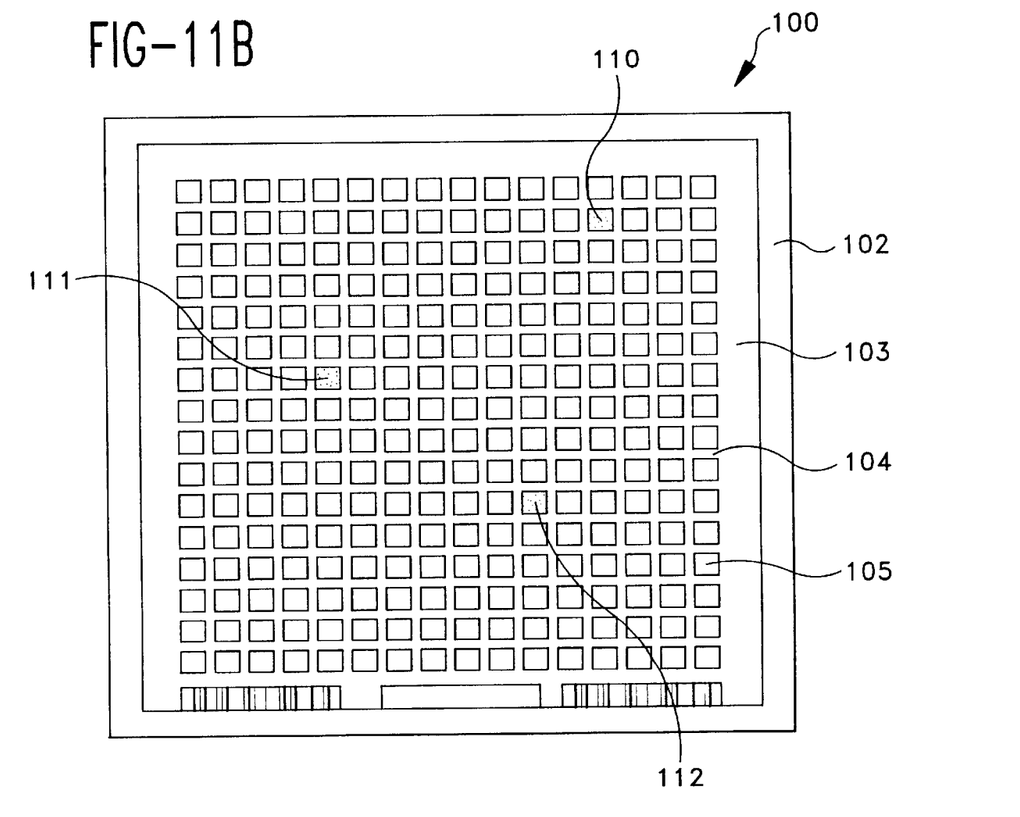
FIG. 11B shows a bottom view of the container shown in FIG. 11A after being inoculated and incubated.

FIG. 11B depicts a bottom view of an inoculated sample container 100, as seen by the CCD camera. A regular pattern of partial samples 105 shows three samples 110, 111, 112 emitting an increased fluorescence intensity, relative to their neighbors. In these three partial samples 110, 111 and 112, microorganisms are present. All the others partial samples do not contain microorganisms and act as "reference samples," which display all the artifacts that are caused by the instrument and sample aging. For example, the so-called "blood-background effect" and the effects of production-related lot-to-lot variations in the fluorescent chemical sensor. Due to the fact that in an apparatus according to the present invention only spacial differences in the fluorescence intensity are indicative of bacterial growth, all the artifacts are canceled out, and significantly improved fluorescence intensity resolution becomes practical. All of this results in a second reduction of the TTD.

Figure 12A:
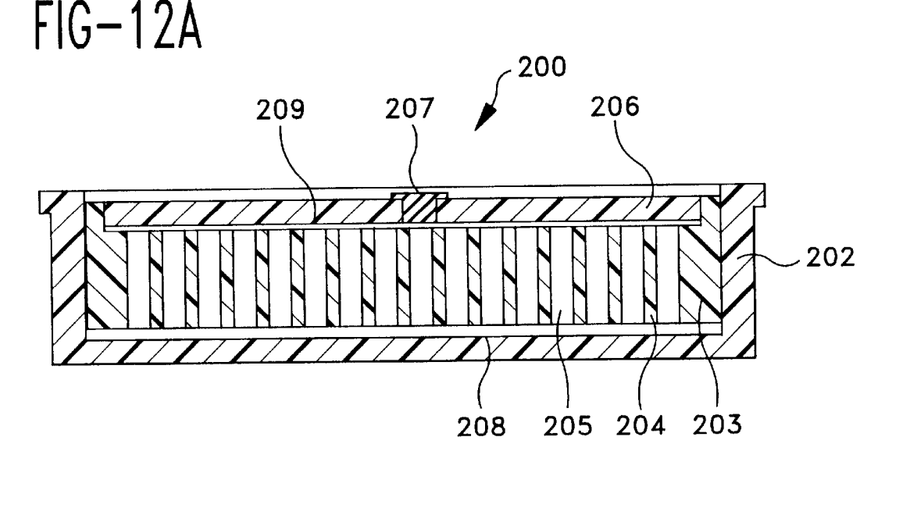
FIG. 12A shows a cross-section of an empty sample container designed for scattered photon migration.

A sample container according to the present invention is not restricted to the use of fluorescent chemical sensors. FIG. 12A shows an example wherein scattered photon migration is used to interrogate a multitude of partial blood samples for the presence of bacteria. In this case, sample container 200 does not contain any sensor. Cover plate 206 is optically transparent, and container 200 is illuminated from above with light in the red spectral region. FIG. 11B depicts a bottom view of an inoculated sample container 200, as seen by a CCD camera. The regular pattern of partial samples shows three samples 210, 211 and 212 emitting a decreased intensity of red light, relative to their neighbors. In these three partial samples, microorganisms are present.

Figure 12B:
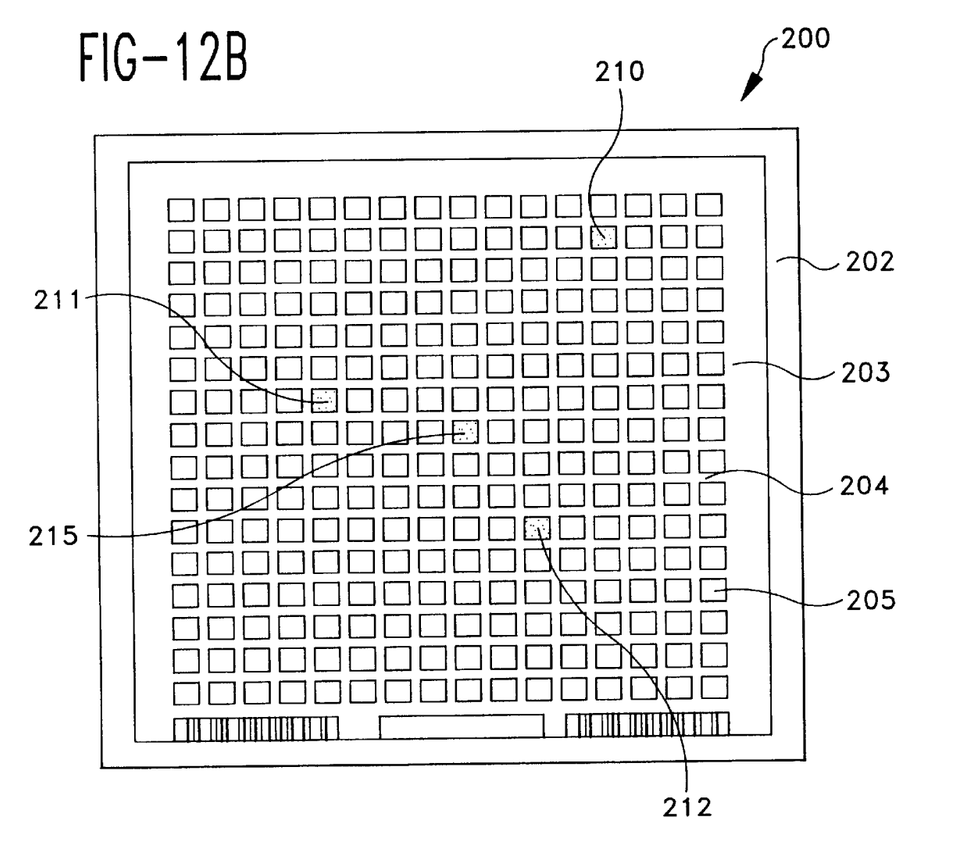
FIG. 12B shows a bottom view of the container shown in FIG. 12A after being inoculated and incubated.

The fourth dark spot 215 at the center of the array is caused by opaque rubber septum 207 in cover plate 206. This central spot is present in all sample containers designed for using scattered photon migration. The location of this spot within the two-dimensional array of partial samples is well-defined and, therefore, this spot can be excluded from the analysis process by applying appropriate software measures.

It has to be re-emphasized that a sample container according to the present invention allows for compensating almost all instrument-, sensor-, and sample-related artifacts due to the many partial "reference samples" being used. As an example of such artifacts, we will discuss door openings for the purpose of loading and unloading of sample containers.

In common blood culture and TB instruments, door openings represent a serious problem. As a consequence of the door opening, warm air is escaping from the interior which results in a major temperature change inside the instrument. This major temperature change, in turn, is acting on the sample containers and causes a more or less pronounced temperature change at the chemical sensor inside the sample containers.

Most sensors respond to temperature changes with a variation in the output signal. It is therefore necessary to interrupt the process of data acquisition for the whole instrument during the door opening and for a certain time interval after the door opening. This time interval is in the order of 0.5 to 1 hour, depending on the particular instrument and sensor design. Interrupting the data acquisition sequence results in difficulties in applying sensitive detection algorithms for the presence of microorganisms. Overall, the TTD will increase, and the probability for errors in detecting the presence or absence of microorganisms will also increase.

In contrast to common instruments, door openings have almost no effect in an instrument according to the present invention. A door opening will also cause a more or less pronounced temperature change in a sample container according to the present invention, however, this will result in a more or less homogeneous temperature change across the entire array of partial samples. Since a homogeneous temperature change is compensated due to the existence of the partial "reference samples," in which the partial sensors respond to the temperature change in the same way as the partial sensors do in subunits showing microorganism growth, no problems occur.

Any inhomogenous temperature change will always show low "spatial frequencies," i.e., the spacial temperature distribution across the array of partial samples is varying slowly with distance. In contrast to this, microorganism growth in isolated partial samples will always generate high "spatial frequencies," i.e., the sensor signal will change from one subunit to the next. Therefore, temperature-related artifacts can be eliminated by applying the method of spatial frequency filtering, which is well-known in the field of electronic image processing. In other words, the image generated by the CCD camera is inspected for intensity changes that occur over a characteristic distance in the order of the diameter of a partial sample. Sensor signal changes that occur over larger distances are excluded. In this way, a very high sensor signal resolution becomes practical, which results in a TTD reduction. Similar considerations apply to all other artifacts mentioned above.

Figure 13:
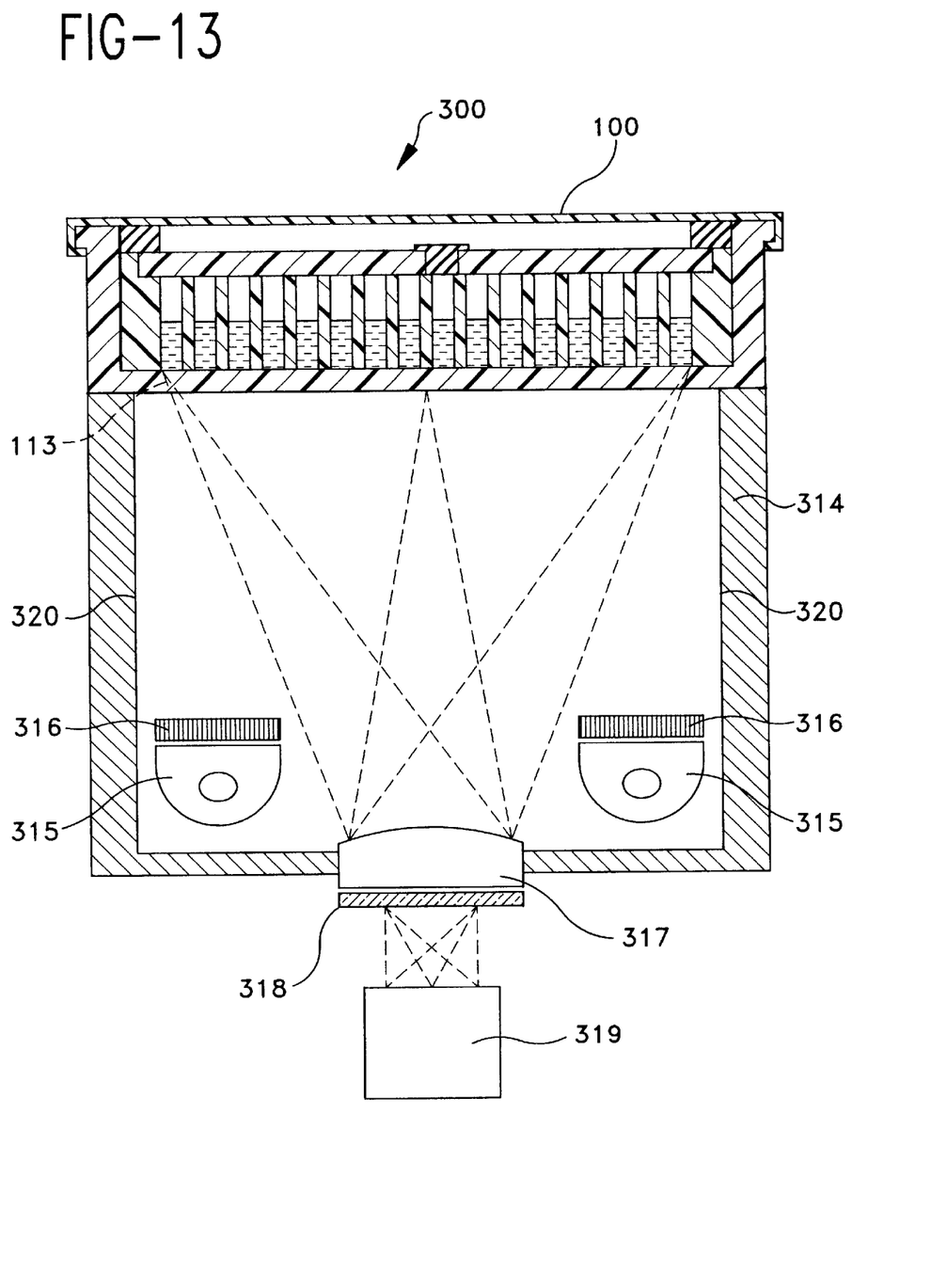
FIG. 13 shows an apparatus for detecting microorganisms according to the present invention.

FIG. 13 illustrates schematically an apparatus 300 for detecting microorganisms according to the present invention. A sample container 100 comprising a fluorescent chemical sensor 13 is shown resting horizontally on an enclosure 314 with highly scattering inner surfaces 320. Fluorescent sensor 113 in container 100 is illuminated with an excitation light by means of an array of excitation light sources 315, with excitation filters 316 arranged between sources 315 and sensor 113. Due to the fact that highly scattering inner surfaces 320 are present, sensor 113 receives an almost evenly distributed excitation intensity.

The whole area covered by sensor 113 and comprising the array of partial sensors is imaged onto an intensified CCD camera 319 by means of an optical system 317. An emission filter 318 is arranged between optical systems 317 and CCD camera 319. The intensified CCD camera 319 is comprised of an ordinary CCD camera and an image intensifier, preferably fiber-coupled to the CCD target. The optoelectronic detection sensitivity of the CCD camera is increased substantially by the image intensifier which results in an improved signal-to-noise ratio, allowing for very high fluorescence intensity resolution.

According to the present invention, all partial samples are arranged in a spacial array, which can be linear, circular, rectangular, hexagonal, statistically distributed, or have other forms. The sensor signals of all partial samples are compared with each other, either visually or by means of an instrument with microorganism growth in one or more than one partial sample causing a change in a sensor signal, relative to partial samples that do not contain microorganisms. A whole sample is considered positive if at least one partial sample generates a sensor signal that is different from the signals generated by its neighbors. In this way, measurement of sensor signal versus time is transferred into measurement of sensor signal versus distance.

In an apparatus according to the present invention, it is not necessary to execute measurements of the sensor signals versus distance at regular time intervals. Therefore, it becomes much easier to check so-called "delayed" samples for positivity. In fact, a sample that became positive before arriving at the blood culture instrument, generates a permanent intensity-versus-distance pattern that can be read out at any time.

The concept of the present invention is not limited to chemical sensors that are based on fluorescence, absorption, colorimetry, or scattered photon migration. The concept of dividing the whole sample into partial samples, with the number of partial samples being larger than the number of microorganisms expected within the whole sample, and comparing the sensor signals of the partial samples with each other, can also be applied if other microorganism sensing principles are utilized. It would be possible, e.g., to equip all the partial samples with a pair of electrodes and to monitor the impedance. In known impedance monitoring instruments, artifacts such as electrode polarization and temperature changes cause very serious detection problems, which is one of the reasons why impedance monitoring has not found widespread application.

In an impedance-monitoring apparatus according to the present invention, all artifacts are canceled out because of the existence of so many reference cells. In a real-life situation in a hospital, no reference samples are available for conventional impedance monitoring, because the patient is either sick or healthy. In an apparatus according to the present invention, a sufficient number of reference samples is generated by splitting the whole sample into a number of partial samples that is larger than the number of organisms. In other words, in all distributions used, the existing organisms will occupy some partial sample chambers and there will be some that will not receive any organism.

It is also possible to equip each partial sample with at least two different sensing means, which allows microorganism identification to be performed, in addition to detection, by analyzing the different sensor data. It has been found that each microorganism species generates different signal-versus-time patterns. Therefore, organism identification can be achieved for the positive partial samples by comparing the patterns acquired via at least two different sensing means with a data base. Such a data base can be created by inoculating known microorganisms in "seeded cultures," and by storing the signal-versus-time patterns.

Figure 14:
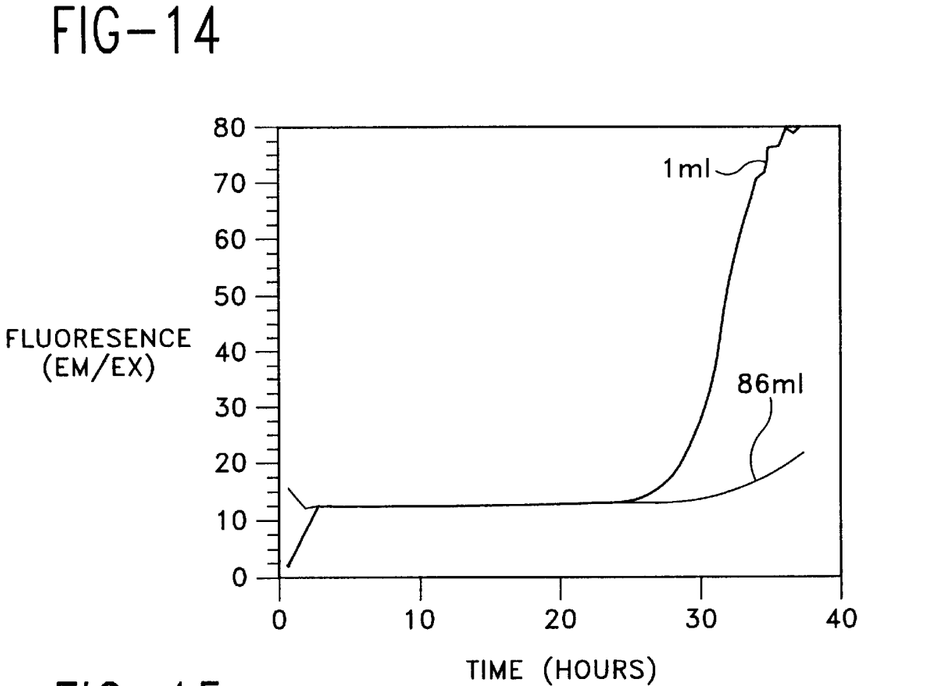
FIG. 14 shows an experimental result illustrating the reduction in TTD due to a smaller sample volume.

FIG. 14 shows an experimental result illustrating the reduction in TTD due to a smaller sample volume. In this case, an equal number of organisms had been inoculated in a standard blood culture vial of 86 ml volume, and in a much smaller vial of only 1 ml volume. As can be seen from this figure, the TTD is reduced from approximately 35 hours in the standard vial down to 25 hours in the smaller vial.

Figure 15:
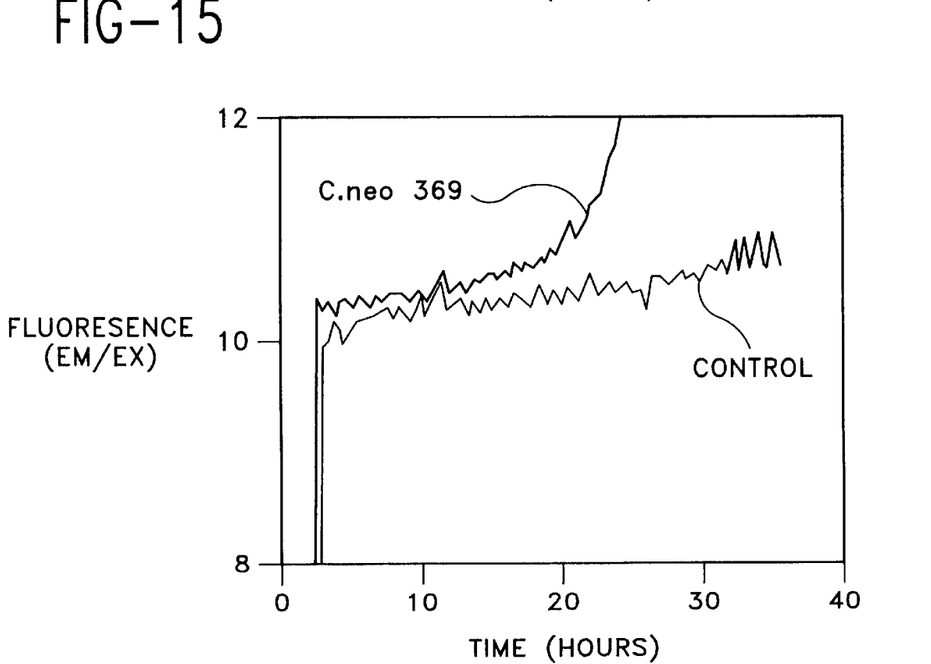
FIG. 15 shows an experimental result illustrating the reduction in TTD by comparing the sensor signals of two partial samples.

FIG. 15 shows an experimental result illustrating the reduction in TTD by comparing the sensor signals of two partial samples. Here, the positive partial sample from FIG. 14 is compared with a negative partial sample of 1 ml volume. After approximately 12 hours, there is a clear differentiation visible between the two sensor signals. In other words, the original TTD for the standard vial, 35 hours, has been reduced to 12 hours. With $V_O$=86 ml and V=1 ml, equation (4) yields N=86, and equation (6) yields n=$\sqrt{86}$=9.3 for the effective number of rows. Based on FIG. 1, the volume splitting is expected to reduce a TTD of 35 hours to approximately 24 hours. Finally, FIG. 2 indicates that a TTD of 24 hours is expected to be reduced to approximately 15.8 hours due to the increased sensor signal resolution. Therefore, the observed reduction in TTD is in very good agreement with that calculated.

After one or more partial samples have become positive there is a need to extract sample material in order to perform consecutive post detection steps such as antimicrobial susceptibility testing. Sample extraction is made easier by modifying cover plate 6 in the embodiments shown in FIGS. 8, 10, 11 and 12. In the embodiment 400, shown in FIG. 16, the cover plate is a bi-layer device. The lower layer 450 is made out of an elastic or plastic material and the upper layer 451 is made out of a form-stable material and both layers are connected together by means of a self-adhesive material. The upper layer 451 acts as a stabilizer and has one small opening for each of the through holes in block 403. This allows one to enter every partial sample with a syringe.

Figure 16:
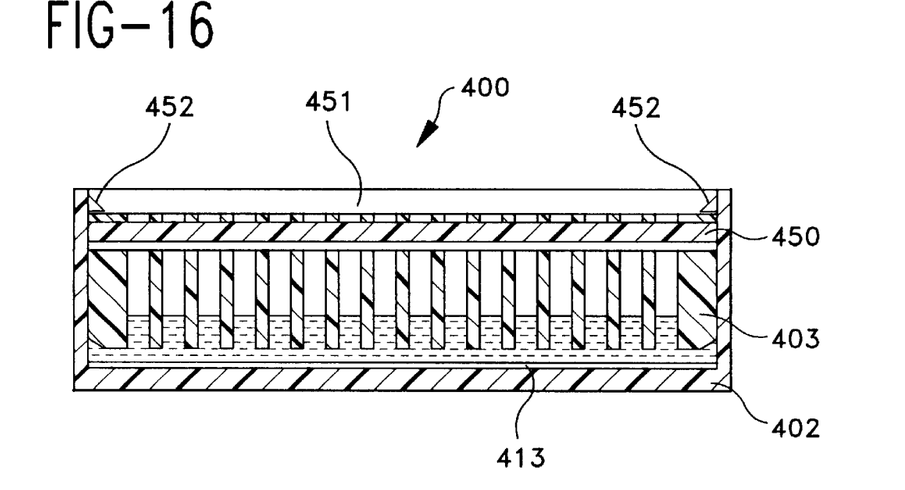
FIG. 16 shows an alternative embodiment of a sample container according to the present invention.

In the sample container 400, shown in FIG. 16, the optically transparent container 402 is made out of a form-stable plastic material. A fluorescent chemical sensor 413 is disposed to the inner bottom, and the container is equipped with a first series of clamps 452 that keep upper layer 451 in its initial position.

Figure 17:
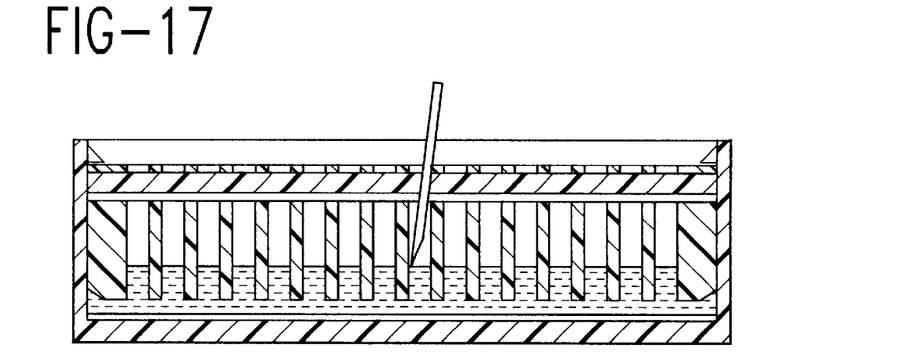
FIG. 17 shows the alternative sample container during the process of injecting the sample.
Figure 18:
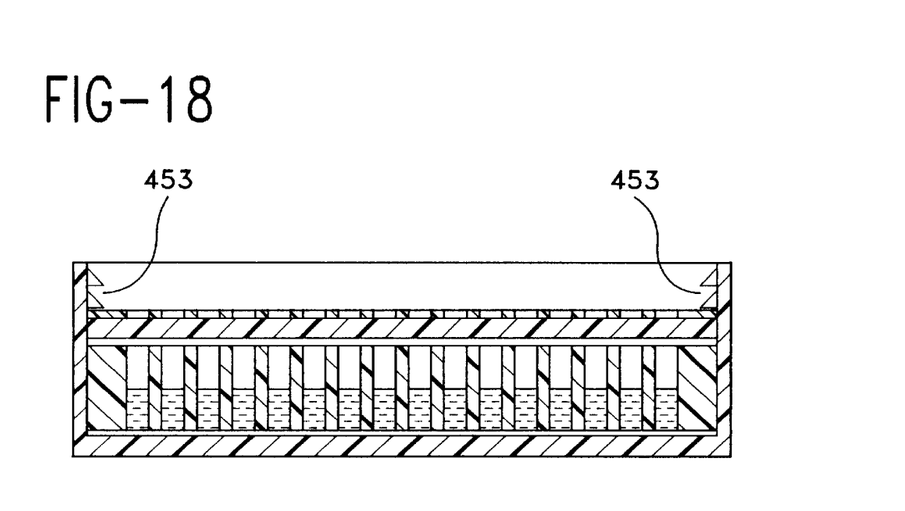
FIG. 18 shows the alternate sample container after injecting the sample and applying an external force to split the sample.

FIG. 17 shows the sample container 400 during the process of injecting a sample, and FIG. 18 depicts the same container after injecting the sample and applying an external force to split the sample. In FIG. 18, a second series of clamps 453 can be seen that hold upper layer 451 in its final position. Due to the fact that many fluorescent sensors involve elastic materials such as silicone rubber, block 403 in the embodiment shown in FIG. 18 does not need to be flexible.

The following Table 1 shows preliminary results obtained using a sample container and apparatus according to the present invention. The table lists the observed time to detection (TTD) in hours for samples monitored on a conventional automated blood culture instrument, and on a sample and apparatus according to the present invention.

TABLE 1

| Sample # | Organism | TTD Conventional Instrument | TTD Present Invention Instrument |
|---|---|---|---|
| 1 | *Haemophilus influenzae* | 21.3 | <12.0 |
| 2 | *Haemophilus influenzae* | 22.0 | <12.0 |
| 3 | *Streptococcus pneumoniae* | 27.7 | <12.0 |
| 4 | *Streptococcus pneumoniae* | 28.1 | <12.0 |
| 5 | *Corynebacterium jeikeium* | 27.8 | <12.0 |
| 6 | *Corynebacterium jeikeium* | 30.1 | <12.0 |
| 7 | *Cryptococcus neoformans* | 53.6 | <17.0 |
| 8 | *Cryptococcus neoformans* | 52.1 | <17.0 |

What is claimed is:

1. An apparatus for detecting microorganisms comprising:
   a container for containing a specimen from a single patient and a culture medium, said container having an inner bottom surface;
   a block movably mounted inside said container and having a plurality of through holes separated by a plurality of inner walls and arranged in a pattern, said block being movable inside said container from a first position to a second position, wherein when said block is in said first position a first gap remains between the bottom of said block and the inner bottom surface of said container; and
   a movable cover plate having a rubber-like septum pressed into said container to prevent gas exchange between the inside of said container and the exterior of said container, said cover plate being movable from a first position to a second position, wherein when said cover plate is in said first position a second gap remains between said cover plate and the top of said block and the specimen from the single patient is injected into said container, and further wherein movement of said cover plate to said second position causes said block to move from said first position to said second position and presses the specimen from the single patient into each of said plurality of through holes to form a plurality of separated partial specimens from the single patient.

2. An apparatus according to claim 1, wherein said container is optically transparent.

3. An apparatus according to claim 2, further comprising:

a chemical sensor inside said container;

means for illuminating said chemical sensor with excitation light by means of an array of excitation light sources to ensure that said chemical sensor receives an almost evenly distributed excitation intensity value;

an optical system for capturing an image of said chemical sensor while said chemical sensor is being excited by said excitation light intensity value; and means for analyzing said captured image which corresponds to a spacial array of partial samples to detect microorganisms in one or more of said plurality of partial samples.

4. An apparatus according to claim 3 wherein said block is made of an elastic material.

5. An apparatus according to claim 3, wherein said block is made of a form-stable material.

6. An apparatus according to claim 3, further comprising a sensor evenly disposed on said inner bottom surface of said optically transparent container, said sensor interrogating said sample container for microorganism growth when illuminated by said excitation intensity and analyzed by said analyzing means.

7. An apparatus according to claim 6, wherein said sensor is based on fluorescence.

8. An apparatus according to claim 6, wherein said sensor is based on absorption.

9. An apparatus according to claim 6, wherein said sensor is based on color imagery.

10. An apparatus according to claim 6, wherein said sensor is based on scattering.

* * * * *